(12) United States Patent
Li et al.

(10) Patent No.: US 11,372,071 B2
(45) Date of Patent: Jun. 28, 2022

(54) METHOD AND SYSTEM FOR DIFFUSION MAGNETIC RESONANCE IMAGING

(71) Applicant: SHANGHAI UNITED IMAGING HEALTHCARE CO., LTD., Shanghai (CN)

(72) Inventors: Guobin Li, Shanghai (CN); Nan Liu, Shanghai (CN); Zhaopeng Li, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

(21) Appl. No.: 17/088,630

(22) Filed: Nov. 4, 2020

(65) Prior Publication Data

US 2021/0048499 A1 Feb. 18, 2021

Related U.S. Application Data

(63) Continuation of application No. PCT/CN2019/080481, filed on Mar. 29, 2019.

(51) Int. Cl.
*G01R 33/565* (2006.01)
*G01R 33/56* (2006.01)
*G01R 33/563* (2006.01)

(52) U.S. Cl.
CPC ... *G01R 33/56545* (2013.01); *G01R 33/5608* (2013.01); *G01R 33/56341* (2013.01)

(58) Field of Classification Search
CPC .......... G01R 33/56545; G01R 33/5608; G01R 33/56341
See application file for complete search history.

(56) References Cited

U.S. PATENT DOCUMENTS

2007/0223832 A1   9/2007  Matsumoto
2011/0052031 A1*  3/2011  Feiweier .......... G01R 33/56518
                                                    382/131

(Continued)

FOREIGN PATENT DOCUMENTS

CN   104574298 A   4/2015
CN   107589387 A   1/2018

OTHER PUBLICATIONS

International Search Report in PCT/CN2019/080481 dated Dec. 27, 2019, 5 pages.

(Continued)

*Primary Examiner* — G. M. A Hyder
(74) *Attorney, Agent, or Firm* — Metis IP LLC

(57) ABSTRACT

A method may include obtaining a plurality of groups of imaging data. Each group of the plurality of groups of imaging data may be generated based on MR signals acquired by an MR scanner via scanning a subject using a diffusion sequence. The method may also include determining one or more correction coefficients associated with an error caused by the diffusion sequence for each group of the plurality of groups of imaging data. The method may also include determining, based on the one or more correction coefficients corresponding to the each group of the plurality of groups of imaging data, a plurality of groups of corrected imaging data. The method may further include determining averaged imaging data by averaging the plurality of groups of corrected imaging data in a complex domain and generating, based on the averaged imaging data, an MR image.

18 Claims, 9 Drawing Sheets

(56) References Cited

U.S. PATENT DOCUMENTS

| | | |
|---|---|---|
| 2011/0085722 A1 | 4/2011 | Feiweier |
| 2015/0212181 A1 | 7/2015 | Liu et al. |
| 2015/0316635 A1 | 11/2015 | Stehning et al. |
| 2020/0029854 A1* | 1/2020 | Nickel ................. G01R 33/565 |

OTHER PUBLICATIONS

Written Opinion in PCT/CN2019/080481 dated Dec. 27, 2019, 5 pages.

* cited by examiner

Image 1          Image 2

Image 1          Image 2

METHOD AND SYSTEM FOR DIFFUSION MAGNETIC RESONANCE IMAGING

CROSS-REFERENCE TO RELATED APPLICATIONS

This application is a continuation of International Application No. PCT/CN2019/080481, filed on Mar. 29, 2019, the entire contents of which are hereby incorporated by reference.

TECHNICAL FIELD

This disclosure generally relates to methods and systems for magnetic resonance imaging (MRI), and more particularly, to methods and systems for diffusion MRI.

BACKGROUND

Magnetic resonance imaging (MRI) is a medical imaging technique used in medical diagnose. Magnetic resonance (MR) scanners use strong magnetic fields, magnetic field gradients, and radio waves to generate images of an object to be scanned (e.g., tissue or organs in a body). The diffusion MRI technique is widely used in MR imaging. Using the diffusion MRI technique, MR imaging data (e.g., MR signals) associated with tissue may be acquired based on water diffusion via applying a diffusion gradient. However, MR imaging data so acquired are sensitive to water diffusion through signal attenuation, which may increase noises in the MR imaging data and decrease the signal to noise ratio (SNR). The water diffusion may be defined by a diffusion sensitivity coefficient (i.e., b value). The greater the diffusion sensitivity coefficient is, the greater the signal attenuation may be, the more noises in the MR imaging data may be, and the smaller the signal to noise ratio (SNR) may be. However, the greater the diffusion sensitivity coefficient is, the higher a contrast between different types of tissue may be. Thus, it is desirable to provide systems and methods for reconstructing MR images with improved SNR and a high b value.

SUMMARY

In some aspects of the present disclosure, a system for magnetic resonance imaging (MRI) is provided. The system may include at least one storage device storing executable instructions, and at least one processor in communication with the at least one storage device. When the least one processor executes the executable instructions, the at least one processor may be configured to cause the system to perform one or more of the following operations. The at least one processor may obtain a plurality of groups of imaging data. Each group of the plurality of groups of imaging data may be generated based on MR signals acquired by an MR scanner via scanning a subject using a diffusion sequence. For each group of the plurality of groups of imaging data, the at least one processor may determine one or more correction coefficients associated with an error caused by the diffusion sequence. The at least one processor may also determine, based on the one or more correction coefficients corresponding to the each group of the plurality of groups of imaging data, a plurality of groups of corrected imaging data. The at least one processor may also determine averaged imaging data by averaging the plurality of groups of corrected imaging data in a complex domain. And the at least one processor may further generate, based on the averaged imaging data, an MR image.

In some embodiments, the one or more correction coefficients may include at least one of a phase correction coefficient configured to correct a phase error or a magnitude correction coefficient configured to correct a magnitude error.

In some embodiments, to determine, based on the one or more correction coefficients corresponding to the each group of the plurality of groups of imaging data, a plurality of groups of corrected imaging data, the at least one processor may be further configured to cause the system to perform additional operations including: performing a dot product between the each group of the plurality of groups of imaging data and the one or more corresponding correction coefficients in an image domain.

In some embodiments, to determine, based on the one or more correction coefficients corresponding to the each group of the plurality of groups of imaging data, a plurality of groups of corrected imaging data, the at least one processor may be further configured to cause the system to perform additional operations including: performing a convolution operation between the each group of the plurality of groups of imaging data and the one or more corresponding correction coefficients in a k-space domain.

In some embodiments, to determine one or more correction coefficients, the at least one processor may be directed to cause the system to perform additional operations including: determining one group of the plurality of groups of imaging data as reference imaging data; determining phase difference data between the each group of the plurality of groups of imaging data and the reference imaging data; and determining, based on the phase difference data, the phase correction coefficient.

In some embodiments, to determine one group of the plurality of groups of imaging data as reference imaging data, the at least one processor may be directed to cause the system to perform additional operations including: identifying the one group of the plurality of groups of imaging data that corresponds to a maximum magnitude among the plurality of groups of imaging data as the reference imaging data.

In some embodiments, to determine, based on the phase difference data, the phase correction coefficient, the at least one processor may be further configured to cause the system to perform additional operations including: performing a lowpass filtering operation on the phase difference data to obtain filtered phase difference data; and designating the filtered phase difference data as the phase correction coefficient.

In some embodiments, to determine one or more correction coefficients, the at least one processor may be directed to cause the system to perform additional operations including: determining one group of the plurality of groups of imaging data as reference imaging data; determining similarity data between the each group of the plurality of groups of imaging data and the reference imaging data; and determining, based on the similarity data, the magnitude correction coefficient.

In some embodiments, to determine one group of the plurality of groups of imaging data as reference imaging data, the at least one processor may be directed to cause the system to perform additional operations including: identifying the one group of imaging data that corresponds to a maximum magnitude among the plurality of groups of imaging data as the reference imaging data.

In some embodiments, to determine one group of the plurality of groups of imaging data as reference imaging data, the at least one processor is directed to cause the system to perform additional operations including: determining an average of magnitude data associated with the plurality of groups of imaging data; and designating the average of the magnitude data associated with the plurality of groups of imaging data as the reference imaging data.

In some embodiments, the at least one processor may be further configured to cause the system to perform additional operations including: performing a lowpass filtering operation on the magnitude correction coefficient; and determining, based on the filtered magnitude correction coefficient, the similarity data.

In some embodiments, the diffusion sequence may include at least one diffusion block associated with a diffusion gradient and at least one imaging block associated with one or more scanning parameters, the imaging block being arranged subsequent to the diffusion block in the diffusion sequence.

In some aspects of the present disclosure, a system for magnetic resonance imaging (MRI) is provided. The system may include at least one storage device storing executable instructions, and at least one processor in communication with the at least one storage device. When the least one processor executes the executable instructions, the at least one processor may be configured to cause the system to perform one or more of the following operations. The at least one processor may obtain a plurality of groups of imaging data, each group being generated via scanning a subject using a diffusion sequence. The at least one processor may determine corrected imaging data by weighting the plurality of groups of imaging data. And the at least one processor may generate a diffusion image of the subject based on the corrected imaging data.

In some embodiments, the weighting may be performed based on a weighting coefficient, the weighting coefficient is determined based on at least one of a phase correction coefficient configured to correct a phase error or a magnitude correction coefficient configured to correct a magnitude error of each group of imaging data.

In some embodiments, at least one of the at least one correction coefficient is determined based on reference imaging data, and the reference imaging data is a group of imaging data that corresponds to a maximum magnitude among the plurality of groups of imaging data, or the reference imaging data is an average of magnitude data associated with the plurality of groups of imaging data.

In some embodiments, the weighting coefficient includes a plurality of weighting factors, each of the plurality of weighting factors corresponding to a pixel of each of the plurality of groups of imaging data, and the greater a similarity between the pixel of each of the plurality of groups of imaging data and a corresponding pixel of the reference imaging data is, the greater a weighting factor corresponding to the pixel is.

In some aspects of the present disclosure, a method for magnetic resonance imaging (MRI) is provided. The method may be implemented on a computing device having one or more processors and one or more storage media. The method may include one or more of the following operations. The method may include obtaining a plurality of groups of imaging data, each group of the plurality of groups of imaging data being generated based on MR signals acquired by an MR scanner via scanning a subject using a diffusion sequence. For each group of the plurality of groups of imaging data, the method may include determining one or more correction coefficients associated with an error caused by the diffusion sequence. The method may include determining, based on the one or more correction coefficients corresponding to the each group of the plurality of groups of imaging data, a plurality of groups of corrected imaging data. The method may include determining averaged imaging data by averaging the plurality of groups of corrected imaging data in a complex domain. And the method may include generating, based on the averaged imaging data, an MR image.

In some aspects of the present disclosure, a method for magnetic resonance imaging (MRI) is provided. The method may be implemented on a computing device having one or more processors and one or more storage media. The method may include one or more of the following operations. The method may include obtaining a plurality of groups of imaging data, each group being generated via scanning a subject using a diffusion sequence. The method may also include determining corrected imaging data by weighting the plurality of groups of imaging data. And the method may further include generating a diffusion image of the subject based on the corrected imaging data.

In some aspects of the present disclosure, a non-transitory computer readable medium is provided. The non-transitory computer readable medium may include a set of instructions for magnetic resonance imaging (MRI). When at least one processor executes the set of instructions, the at least one processor may be directed to perform one or more of the following operations. The at least one processor may obtain a plurality of groups of imaging data, each group of the plurality of groups of imaging data being generated based on MR signals acquired by an MR scanner via scanning a subject using a diffusion sequence. For each group of the plurality of groups of imaging data, the at least one processor may determine one or more correction coefficients associated with an error caused by the diffusion sequence. The at least one processor may determine, based on the one or more correction coefficients corresponding to the each group of the plurality of groups of imaging data, a plurality of groups of corrected imaging data. The at least one processor may determine averaged imaging data by averaging the plurality of groups of corrected imaging data in a complex domain. And the at least one processor may generate, based on the averaged imaging data, an MR image.

In some aspects of the present disclosure, a non-transitory computer readable medium is provided. The non-transitory computer readable medium may include a set of instructions for magnetic resonance imaging (MRI). When at least one processor executes the set of instructions, the at least one processor may be directed to perform one or more of the following operations. The at least one processor may obtain a plurality of groups of imaging data, each group being generated via scanning a subject using a diffusion sequence. The at least one processor may determine corrected imaging data by weighting the plurality of groups of imaging data. And the at least one processor may generate a diffusion image of the subject based on the corrected imaging data.

In some aspects of the present disclosure, a system for magnetic resonance imaging (MRI) is provided. The system may include an obtaining module, a correction module, an averaging module, and a generation module. The obtaining module may be configured to obtain a plurality of groups of imaging data. Each group of the plurality of groups of imaging data may be generated based on MR signals acquired by an MR scanner via scanning a subject using a diffusion sequence. The correction module may be configured to determine one or more correction coefficients associated with an error caused by the diffusion sequence for each group of the plurality of groups of imaging data, and determine a plurality of groups of corrected imaging data based on the one or more correction coefficients corresponding to the each group of the plurality of groups of imaging data. The averaging module may be configured to determine averaged imaging data by averaging the plurality of groups of corrected imaging data in a complex domain. And the generation module may be configured to generate, based on the averaged imaging data, an MR image.

In some aspects of the present disclosure, a system for magnetic resonance imaging (MRI) is provided. The system may include an obtaining module, a correction module, and a generation module. The obtaining module may be configured to obtain a plurality of groups of imaging data. Each group may be generated via scanning a subject using a diffusion sequence. The correction module may be configured to determine corrected imaging data by weighting the plurality of groups of imaging data. And the generation module may be configured to generate a diffusion image of the subject based on the corrected imaging data.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but is to be accorded the widest scope consistent with the claims.

It will be understood that the term "system," "engine," "unit," "module," and/or "block" used herein are one method to distinguish different components, elements, parts, section or assembly of different level in ascending order. However, the terms may be displaced by another expression if they may achieve the same purpose.

Figure 2:
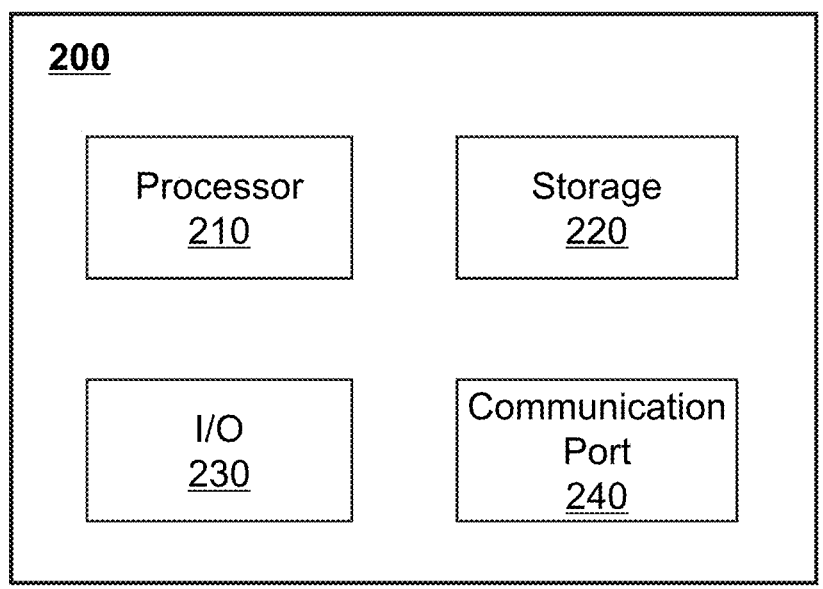
FIG. 2 is a schematic diagram illustrating exemplary hardware and software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an Erasable Programmable Read Only Memory (EPROM). It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments in the present disclosure. It is to be expressly understood, the operations of the flowchart may be implemented not in order. Conversely, the operations may be implemented in inverted order, or simultaneously. Moreover, one or more other operations may be added to the flowcharts. One or more operations may be removed from the flowcharts.

The present disclosure relates to methods and systems for diffusion MR image reconstruction. A system may obtain a plurality of groups of imaging data. Each group of the plurality of groups of imaging data may be generated based on MR signals acquired by an MR scanner via scanning a subject using a diffusion sequence. The system may also determine one or more correction coefficients associated with an error caused by the diffusion sequence for each group of the plurality of groups of imaging data. The correction coefficients may be configured to correct a phase error and/or magnitude error caused by the diffusion sequence. The system may also determine a plurality of groups of corrected imaging data based on the one or more correction coefficients corresponding to the each group of the plurality of groups of imaging data. Each group of the plurality of groups of imaging data may be corrected based on the one or more correction coefficients (e.g., a magnitude correction coefficient). The correction may decrease or remove abnormal signals (e.g., noises) caused by the magnitude error, thereby improving the SNR of the imaging data. Alternatively or additionally, an averaging (i.e., complex domain averaging) may be performed in the complex domain on the plurality of groups of image data (e.g., the plurality of groups of corrected imaging data), which may decrease accumulated noises thereby increasing the SNR of the imaging data. The system may generate a target MR image based on the processed (e.g., corrected and/or average) imaging data.

Figure 1:
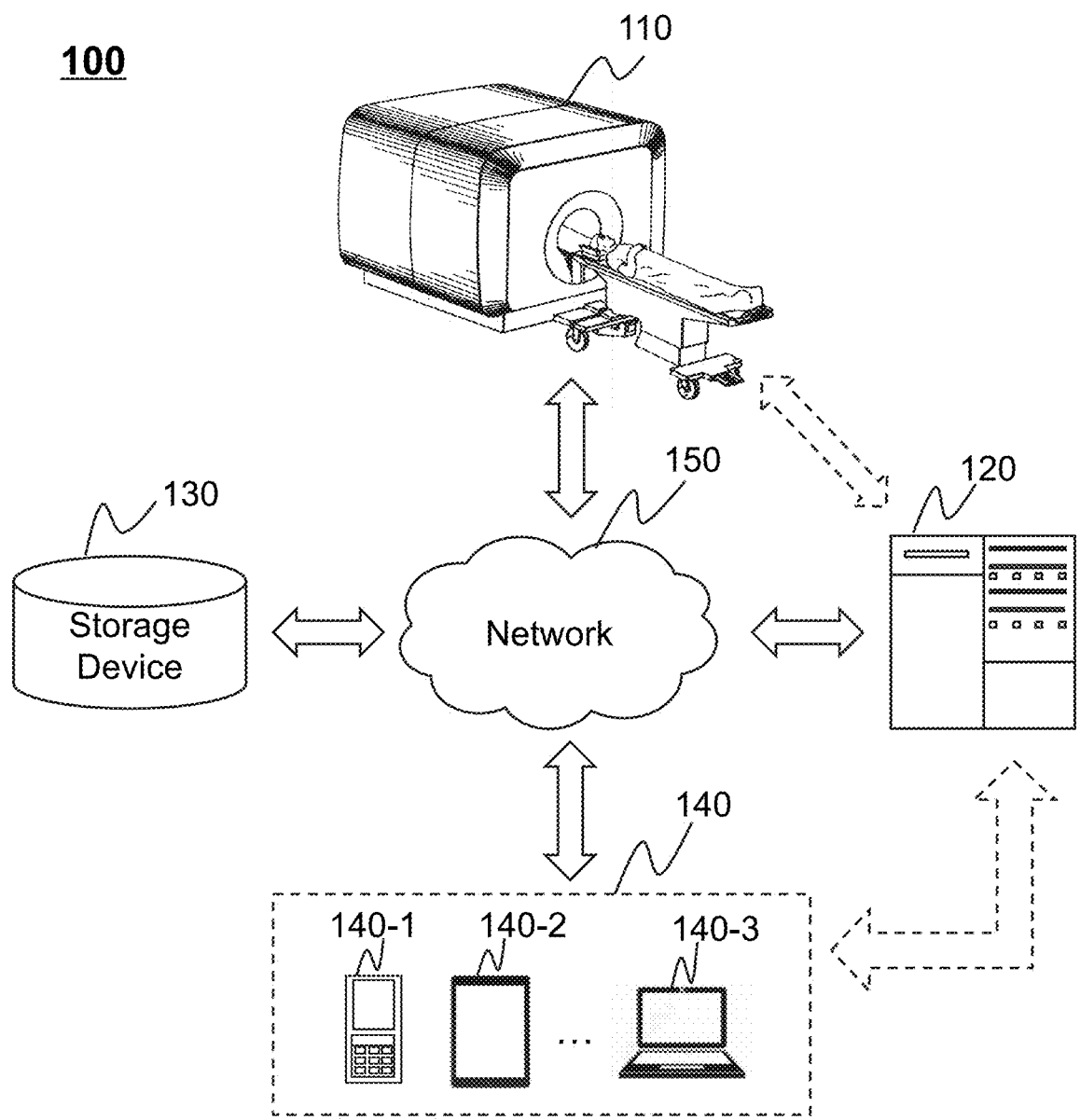
FIG. 1 is a schematic diagram illustrating an exemplary MRI system according to some embodiments of the present disclosure.

FIG. 1 is a schematic diagram illustrating an exemplary MRI system 100 according to some embodiments of the present disclosure. As illustrated, the MRI system 100 may include an MR scanner 110, a processing device 120, a storage device 130, one or more terminals 140, and a network 150. The components in the MRI system 100 may be connected in one or more of various ways. Merely by way of example, as illustrated in FIG. 1, the MR scanner 110 may be connected to the processing device 120 through the network 150. As another example, the MR scanner 110 may be connected with the processing device 120 directly as indicated by the bi-directional arrow in dotted lines linking the MR scanner 110 and the processing device 120. As a further example, the storage device 130 may be connected with the processing device 120 directly (not shown in FIG. 1) or through the network 150. As still a further example, one or more terminal(s) 140 may be connected with the processing device 120 directly (as indicated by the bi-directional arrow in dotted lines linking the terminal(s) 140 and the processing device 120) or through the network 150.

The MR scanner 110 may scan a subject or a portion thereof that is located within its detection region and generate MR signals relating to the (part of) subject. In the present disclosure, the terms "subject" and "object" are used interchangeably. In some embodiments, the subject may include a body, a substance, or the like, or a combination thereof. In some embodiments, the subject may include a specific portion of a body, such as the head, the thorax, the abdomen, or the like, or a combination thereof. In some embodiments, the subject may include a specific organ, such as the heart, the esophagus, the trachea, the bronchus, the stomach, the gallbladder, the small intestine, the colon, the bladder, the ureter, the uterus, the fallopian tube, etc. The MR scanner 110 may include a magnet assembly, a gradient coil assembly, and a radiofrequency (RF) coil assembly.

The magnet assembly may generate a first magnetic field (also referred to as a main magnetic field) for polarizing the subject to be scanned. The magnet assembly may include a permanent magnet, a superconducting electromagnet, a resistive electromagnet, etc.

The gradient coil assembly may generate a second magnetic field (also referred to as a gradient magnetic field). The gradient coil assembly may include X-gradient coils, Y-gradient coils, and Z-gradient coils. The gradient coil assembly may generate one or more magnetic field gradient pulses to the main magnetic field in the X direction (Gx), the Y direction (Gy), and the Z direction (Gz) to encode the spatial information of the subject. In some embodiments, the X direction may be designated as a frequency encoding direction, while the Y direction may be designated as a phase encoding direction. In some embodiments, Gx may be used for frequency encoding or signal readout, generally referred to as frequency encoding gradient or readout gradient. In some embodiments, Gy may be used for phase encoding, generally referred to as phase encoding gradient. In some embodiments, Gz may be used for slice selection for obtaining 2D k-space data. In some embodiments, Gz may be used for phase encoding for obtaining 3D k-space data.

The RF coil assembly may include a plurality of RF coils. The RF coils may include one or more RF transmit coils and/or one or more RF receiver coils. The RF transmit coil(s) may transmit RF pulses to the subject. Under the coordinated action of the main magnetic field, the gradient magnetic field, and the RF pulses, MR signals relating to the subject may be generated according to a pulse sequence. The RF receiver coils may acquire MR signals from the subject according to the pulse sequence. The MR signals may also be referred to as echo signals. The MR signals may be processed using a transform operation (e.g., a Fourier transform) to fill a k-space to obtain k-space data. The pulse sequence may be defined by imaging parameters and arrangement associated with the image parameters in time sequence. For example, the pulse sequence may be defined by one or more parameters relating to time, such as a repetition time (TR), an acquisition time (TA), an echo time (TE), etc. Exemplary pulse sequences may include a spin echo sequence, a gradient echo sequence, a diffusion sequence, an inversion recovery sequence, or the like, or a combination thereof. For example, the spin echo sequence may include a fast spin echo (FSE), a turbo spin echo (TSE), a rapid acquisition with relaxation enhancement (RARE), a half-Fourier acquisition single-shot turbo spin-echo (HASTE), a turbo gradient spin echo (TGSE), or the like, or a combination thereof. The gradient echo sequence may include an echo planar imaging (EPI) sequence. In some embodiments, the pulse sequence may include a diffusion sequence. The diffusion sequence may include at least one diffusion block associated with one or more parameters of a diffusion gradient and at least one imaging block associated with one or more scanning parameters (e.g., parameters associated with one or more encoding gradients applied in a scanning). In some embodiments, the pulse sequence may include a single-shot pulse sequence (e.g., single-shot FSE, single-shot EPI, etc.), multi-shot pulse sequence (e.g., multi-shot FSE, multi-shot EPI, etc.). In some embodiments, for a single-shot pulse sequence (e.g., single-shot FSE, single-shot EPI, etc.), an RF pulse may be applied once within a TR, and one or more echo signals may be sampled within the TR. For a multi-shot pulse sequence (e.g., multi-shot FSE, multi-shot EPI, etc.), an RF pulse may be applied for multiple times within a TR, and one or more echo signals may be sampled during each shot or emission of the RF pulse of the multiple-shot pulse sequence.

In some embodiments, the MR scanner 110 may include an analog-to-digital converter (ADC) (not shown in FIG. 1). The analog-to-digital converter may convert MR signals received by one or more RF receiver coils into MR imaging data. The analog-to-digital converter may be a direct-conversion ADC, a successive-approximation ADC, a ramp-compare ADC, a Wilkinson ADC, an integrating ADC, a delta-encoded ADC, a pipeline ADC, a sigma-delta ADC, or the like, or a combination thereof.

The processing device 120 may process data and/or information obtained and/or retrieve from the MR scanner 110, the terminal(s) 140, the storage device 130 and/or other storage devices. For example, the processing device 120 may obtain a plurality of groups of imaging data and reconstruct a target MR image based on the plurality of groups of imaging data. As a further example, the processing device 120 may determine one or more correction coefficients associated with an error caused by the diffusion sequence for each group of the plurality of groups of imaging data and determine a plurality of groups of corrected imaging data based on the one or more correction coefficients corresponding to the each group of the plurality of groups of imaging data. Then the processing device 120 may determine averaged imaging data by averaging the plurality of groups of corrected imaging data in the complex domain and generate the target MR image based on the averaged imaging data. In some embodiments, a reconstructed image may be transmitted to the terminal(s) 140 and displayed on one or more display devices in the terminal(s) 140. In some embodiments, the processing device 120 may be a single server or a server group. The server group may be centralized or distributed. In some embodiments, the processing device 120 may be local or remote. For example, the processing device 120 may access information and/or data stored in the MR scanner 110, the terminal(s) 140, and/or the storage device 130 via the network 150. As another example, the processing device 120 may be directly connected with the MR scanner 110, the terminal(s) 140, and/or the storage device 130 to access stored information and/or data. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 120 may be implemented on a computing device 200 having one or more components illustrated in FIG. 2 in the present disclosure.

The storage device 130 may store data and/or instructions. In some embodiments, the storage device 130 may store data obtained from the terminal(s) 140 and/or the processing device 120. For example, the storage device 130 may store a plurality of groups of imaging data (e.g., k-space data, MR images), intermediate data generated in an MR image reconstruction (e.g., one or more correction coefficients, corrected imaging data, averaged imaging data), target MR images, etc. In some embodiments, the storage device 130 may store data and/or instructions that the processing device 120 may execute or use to perform exemplary methods described in the present disclosure. In some embodiments, the storage device 130 may include a mass storage device, a removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected with the network 150 to communicate with one or more components of the MRI system 100 (e.g., the processing device 120, the terminal(s) 140, etc.). One or more components of the MRI system 100 may access the data or instructions stored in the storage device 130 via the network 150. In some embodiments, the storage device 130 may be directly connected with or communicate with one or more components of the MRI system 100 (e.g., the processing device 120, the terminal(s) 140, etc.). In some embodiments, the storage device 130 may be part of the processing device 120.

The terminal(s) 140 may include a mobile device 140-1, a tablet computer 140-2, a laptop computer 140-3, or the like, or any combination thereof. In some embodiments, the mobile device 140-1 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a smart bracelet, smart footgear, a pair of smart glasses, a smart helmet, a smartwatch, smart clothing, a smart backpack, a smart accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass, an Oculus Rift, a Hololens, a Gear VR, etc. In some embodiments, the terminal(s) 140 may remotely operate the MR scanner 110. In some embodiments, the terminal(s) 140 may operate the MR scanner 110 via a wireless connection. In some embodiments, the terminal(s) 140 may receive information and/or instructions inputted by a user, and send the received information and/or instructions to the MR scanner 110 or the processing device 120 via the network 150. In some embodiments, the terminal(s) 140 may receive data and/or information from the processing device 120. In some embodiments, the terminal(s) 140 may be part of the processing device 120. In some embodiments, the terminal(s) 140 may be omitted.

In some embodiments, the terminal(s) 140 may send and/or receive information for MR image reconstruction to the processing device 120 via a user interface. The user interface may be in the form of an application for MR image reconstruction implemented on the terminal(s) 140. The user interface implemented on the terminal(s) 140 may be configured to facilitate communication between a user and the processing device 120. In some embodiments, a user may input a request for MR image reconstruction via the user interface implemented on a terminal 140. The terminal(s) 140 may send the request for MR image reconstruction to the processing device 120 for reconstructing an MR image as described elsewhere in the present disclosure (e.g., FIG. 5 and the descriptions thereof). In some embodiments, the user may input and/or adjust scanning or imaging parameters of a pulse sequence via the user interface. In some embodiments, the user interface may facilitate the presentation or display of information and/or data (e.g., a signal) relating to MR image reconstruction received from the processing device 120. For example, the information and/or data may include a result generated by the processing device 120 in an image reconstruction. For example, the result may include one or more images (e.g., 2D images, 3D images, etc.), one or more data figures, one or more words, one or more digits, one or more models for MR image reconstruction, parameters used in such image reconstruction, etc. In some embodiments, the information and/or data may be further configured to cause the terminal(s) 140 to display the result to the user.

The network 150 may include any suitable network that can facilitate the exchange of information and/or data for the MRI system 100. In some embodiments, one or more components of the MRI system 100 (e.g., the MR scanner 110, the terminal(s) 140, the processing device 120, or the storage device 130) may communicate information and/or data with one or more other components of the MRI system 100 via the network 150. For example, the processing device 120 may obtain MR signals from the MR scanner 110 via the network 150. As another example, the processing device 120 may obtain user instructions from the terminal(s) 140 via the network 150. In some embodiments, the network 150 may be any type of wired or wireless network, or a combination thereof. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the MRI system 100 may be connected with the network 150 to exchange data and/or information.

The network 150 may include any suitable network that can facilitate the exchange of information and/or data for the MRI system 100. In some embodiments, one or more components of the MRI system 100 (e.g., the MR scanner 110, the terminal(s) 140, the processing device 120, the storage device 130, etc.) may transmit or receive information and/or data with one or more other components of the MRI system 100 via the network 150. For example, the processing device 120 may obtain imaging data from the MR scanner 110 via the network 150. As another example, the processing device 120 may obtain user instructions from the terminal(s) 140 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the MRI system 100 may be connected with the network 150 to exchange data and/or information.

FIG. 2 is a schematic diagram illustrating hardware and/or software components of an exemplary computing device 200 on which the processing device 120 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (program code) and perform functions of the processing device 120 in accordance with techniques described herein. The computer instructions may include, for example, routines, programs, objects, components, signals, data structures, procedures, modules, and functions, which perform particular functions described herein. For example, the processor 210 may process data obtained from the MR scanner 110, the terminal(s) 140, the storage device 130, and/or any other component of the MRI system 100. Specifically, the processor 210 may process one or more measured data sets obtained from the MR scanner 110. For example, the processor 210 may reconstruct an image based on the data set(s). In some embodiments, the reconstructed image may be stored in the storage device 130, the storage 220, etc. In some embodiments, the reconstructed image may be displayed on a display device by the I/O 230. In some embodiments, the processor 210 may perform instructions obtained from the terminal(s) 140. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the MR scanner 110, the terminal(s) 140, the storage device 130, or any other component of the MRI system 100. In some embodiments, the storage 220 may include a mass storage device, a removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 120 for MR image reconstruction.

The I/O 230 may input or output signals, data, and/or information. In some embodiments, the I/O 230 may enable user interaction with the processing device 120. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected with a network (e.g., the network 150) to facilitate data communications. The communication port 240 may establish connections between the processing device 120 and the MR scanner 110, the terminal(s) 140, or the storage device 130. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
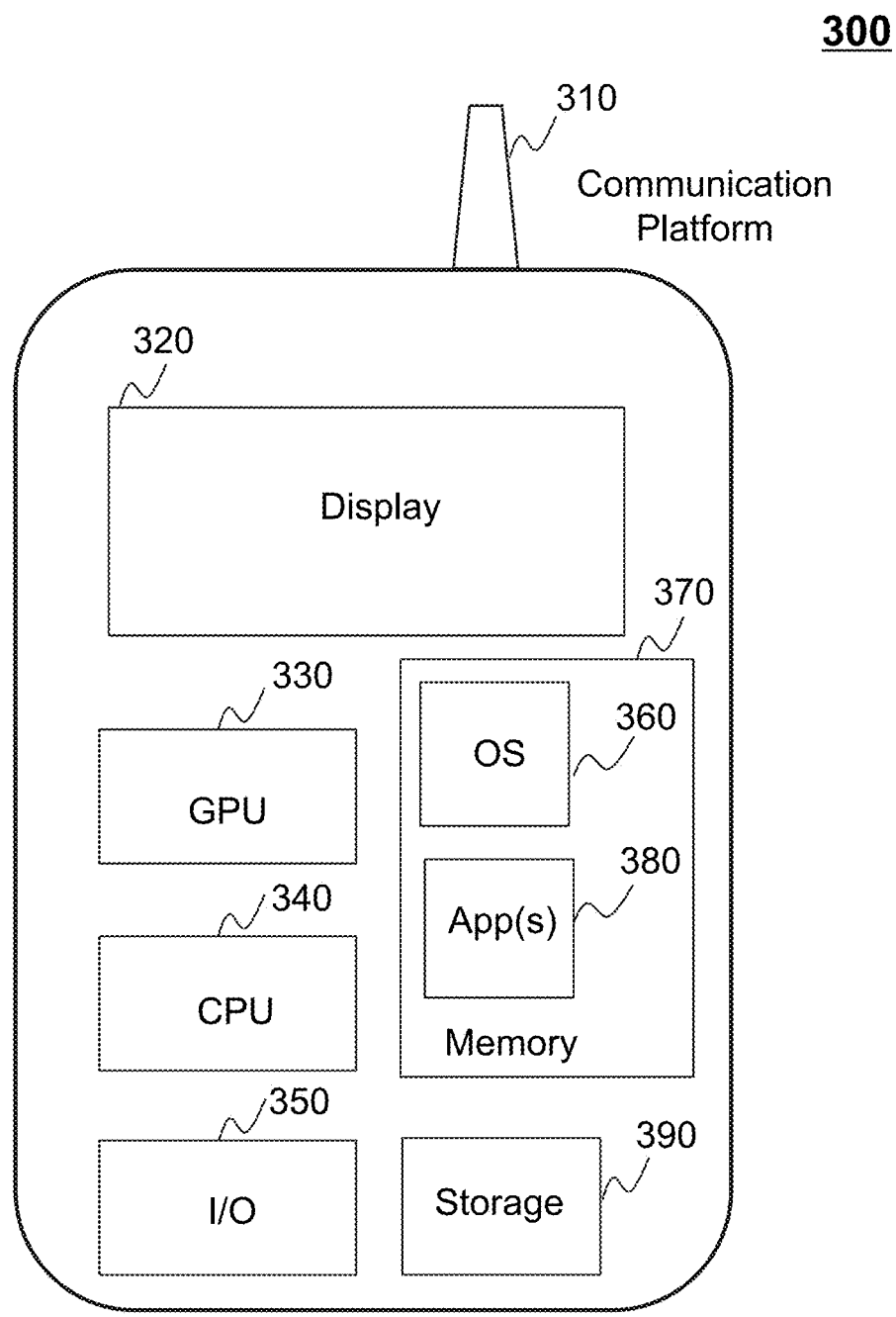
FIG. 3 is a schematic diagram illustrating exemplary hardware and/or software components of an exemplary mobile device according to some embodiments of the present disclosure.

FIG. 3 is a schematic diagram illustrating hardware and/or software components of an exemplary mobile device 300 according to some embodiments of the present disclosure. As illustrated in FIG. 3, the mobile device 300 may include a communication platform 310, a display 320, a graphics processing unit (GPU) 330, a central processing unit (CPU) 340, an I/O 350, a memory 370, and a storage 390. In some embodiments, any other suitable component, including but not limited to a system bus or a controller (not shown), may also be included in the mobile device 300. In some embodiments, a mobile operating system 360 (e.g., iOS, Android, Windows Phone, etc.) and one or more applications 380 may be loaded into the memory 370 from the storage 390 in order to be executed by the CPU 340. The applications 380 may include a browser or any other suitable mobile apps for receiving and rendering information relating to image processing or other information from the processing device 120. User interactions with the information stream may be achieved via the I/O 350 and provided to the processing device 120 and/or other components of the MRI system 100 via the network 150.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate an image as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4:
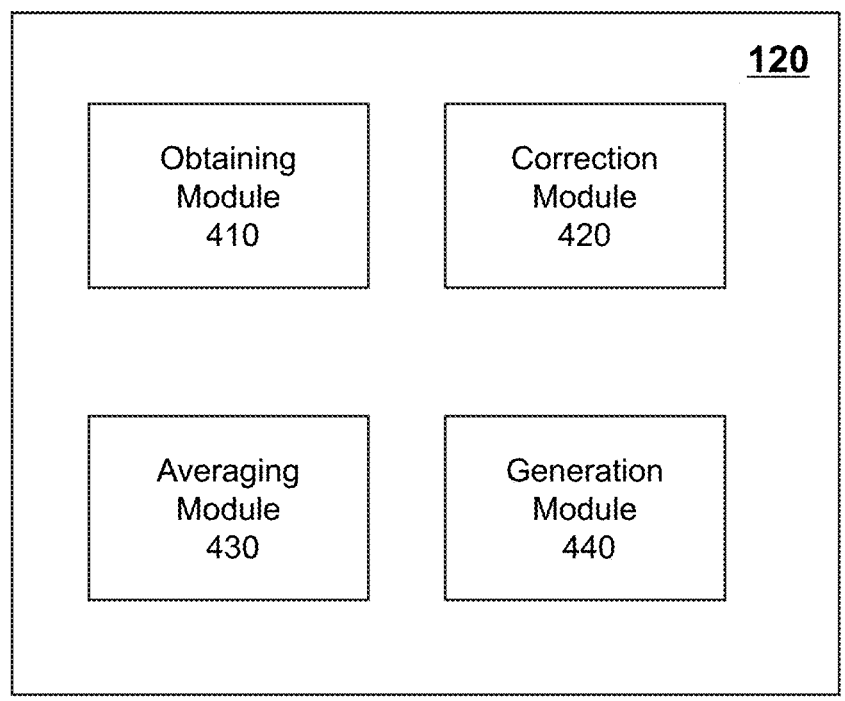
FIG. 4 is a block diagram illustrating an exemplary processing device according to some embodiments of the present disclosure.

FIG. 4 is a block diagram illustrating an exemplary processing device according to some embodiments of the present disclosure. The processing device 120 may include an obtaining module 410, a correction module 420, an averaging module 430, and a generation module 440. One or more of the modules of the processing device 120 may be interconnected. The connection(s) may be wireless or wired. At least a portion of the processing device 120 may be implemented on a computing device as illustrated in FIG. 2 or a mobile device as illustrated in FIG. 3.

The obtaining module 410 may be configured to obtain a plurality of groups of imaging data. Each group of the plurality of groups of imaging data may be generated based on MR signals acquired by an MR scanner via scanning a subject using a diffusion sequence. In some embodiments, the obtaining module 410 may obtain the plurality of groups of imaging data from the MR scanner 110, the storage device 130, or any other storage device as described elsewhere in the present disclosure.

The correction module 420 may be configured to determine one or more correction coefficients associated with an error caused by the diffusion sequence for each group of the plurality of groups of imaging data. Each group of the plurality of groups of imaging data may correspond to one or more correction coefficients. In some embodiments, the correction module 420 may further determine, based on the one or more correction coefficients corresponding to the each group of the plurality of groups of imaging data, a plurality of groups of corrected imaging data. In some embodiments, the correction module 420 may be configured to determine a weighting coefficient corresponding to each group of the plurality of groups of imaging data. The correction module 420 may determine the plurality of groups of corrected imaging data by weighting the plurality of groups of imaging data.

In some embodiments, the plurality of groups of corrected imaging data may be generated in the image domain. For example, the correction module 420 may determine a specific group of corrected imaging data by performing a dot product between the specific group of imaging data and the one or more corresponding correction coefficients. In some embodiments, the plurality of groups of corrected imaging data may be generated in the k-space domain. For example, the correction module 420 may determine a specific group of corrected imaging data by performing a convolution operation between the specific group of imaging data and the one or more corresponding correction coefficients.

The averaging module 430 may be configured to determine averaged imaging data by averaging the plurality of groups of corrected imaging data in the complex domain. In some embodiments, the plurality of groups of corrected imaging data may be in the image domain. For example, each of the plurality of groups of corrected imaging data may include a corrected MR image. The averaging of the plurality of groups of corrected imaging may be performed by averaging the plurality of corrected MR images. In some embodiments, the plurality of groups of corrected imaging data may be in the k-space domain. For example, each of the plurality of groups of corrected imaging data may include corrected k-space data. The averaging module 430 may be configured to convert the corrected k-space data into the corrected MR image by inverse Fourier Transform.

The generation module 440 may be configured to generate a target MR image based on the averaged imaging data. In some embodiments, the generation module 440 may generate the target MR image by converting the averaged imaging data in the k-space domain into the imaging domain. For example, the processing device 120 may perform a Fourier transform on the averaged imaging data in the k-space domain. In some embodiments, the processing device 120 may designate the averaged imaging data in the image domain as the target MR image.

It should be noted that the above description of the processing device 120 is merely provided for the purpose of illustration, and not intended to limit the scope of the present disclosure. For persons having ordinary skills in the art, various variations and modifications may be performed in the light of the present disclosure. However, those variations and modifications do not depart from the scope of the present disclosure. For example, one or more of the modules of the processing device 120 mentioned above may be omitted or integrated into a single module. As another example, the processing device 120 may include one or more additional modules, for example, a storage module for data storage.

Figure 5:
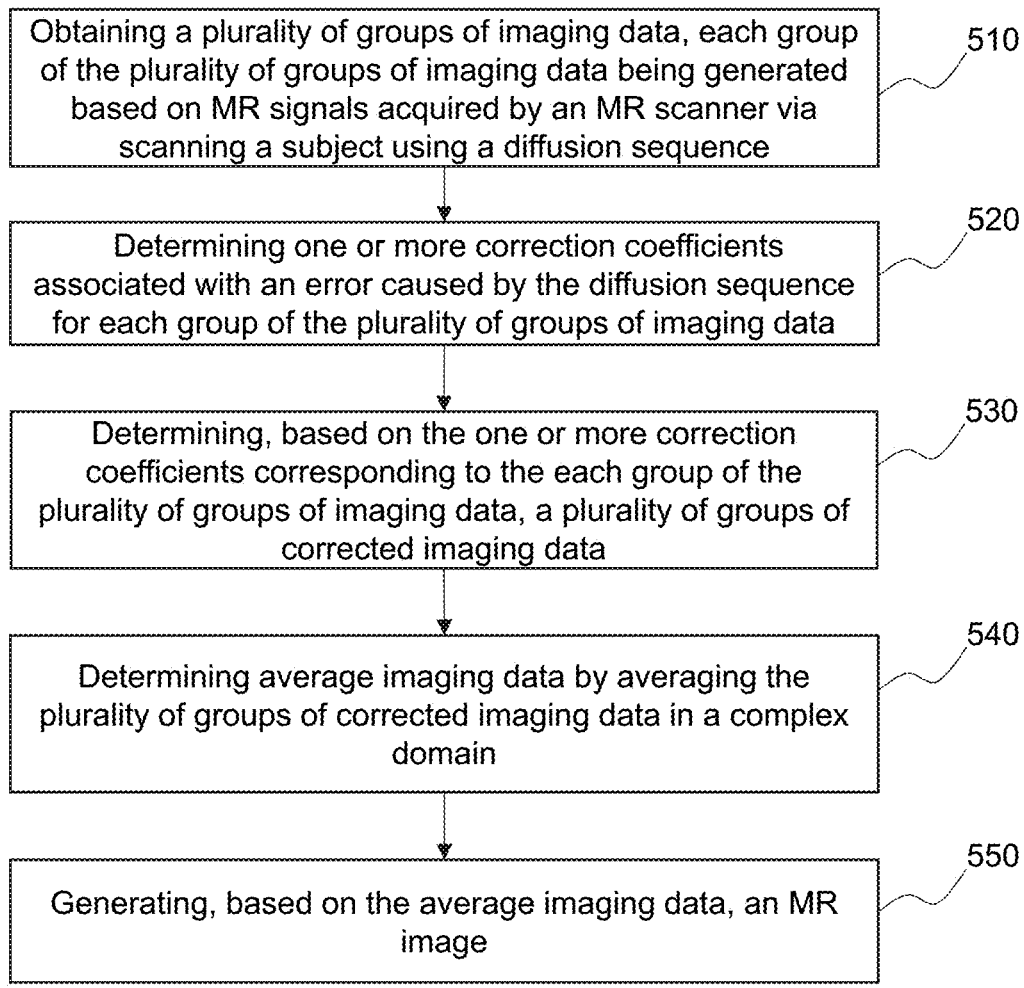
FIG. 5 is a flowchart of an exemplary process for generating an MR image according to some embodiments of the present disclosure.

FIG. 5 is a flowchart of an exemplary process 500 for generating an MR image according to some embodiments of the present disclosure. The process 500 may be executed by the processing device 120. For example, the process 500 may be implemented as a set of instructions (e.g., an application) stored in the storage, e.g., storage 220, the storage device 130, the storage 390, a storage device external to and accessible by the MRI system 100. The processing device 120, the processor 210, and the CPU 340, may execute the set of instructions, and when executing the instructions, it may be configured to perform the process 500. The operations of the process 500 presented below are intended to be illustrative. In some embodiments, the process may be accomplished with one or more additional operations not described, and/or without one or more of the operations discussed. Additionally, the order in which the operations of the process 500 as illustrated in FIG. 5 and described below is not intended to be limiting.

In 510, the processing device 120 (e.g., the obtaining module 410) (e.g., the interface circuits of the processor 210) may obtain a plurality of groups of imaging data. Each group of the plurality of groups of imaging data may be generated based on MR signals acquired by an MR scanner via scanning a subject using a diffusion sequence. In some embodiments, the obtaining module 410 may obtain the plurality of groups of imaging data from the MR scanner 110, the storage device 130, or any other storage device as described elsewhere in the present disclosure.

The diffusion sequence may be used in a diffusion imaging technique. Exemplary diffusion imaging techniques may include a diffusion weighted imaging (DWI) technique, a diffusion tensor imaging (DTI) technique, a diffusion tensor tracking (DTT) imaging technique, etc. The diffusion sequence may include at least one diffusion block associated with a diffusion gradient and at least one imaging block associated with one or more imaging parameters (also referred to as scanning parameters). The at least one imaging block may be arranged subsequent to the diffusion block in the diffusion sequence. The at least diffusion block may be defined by one or more parameters of the diffusion gradient, such as a magnitude of the diffusion gradient, a gradient direction, time for applying the diffusion gradient, a duration for applying the diffusion gradient, etc. The at least one imaging block may be defined by the one or more imaging parameters and sequential and/or temporal arrangement thereof. Exemplary imaging parameters may include parameters relating to gradient fields (e.g., a phase encoding gradient field, a frequency encoding gradient field, etc.) generated by a gradient coil, parameters relating to MR signals (e.g., an echo time (TE), an echo train length (ETL), a spin echo type, the number or count of phases), etc. In some embodiments, the diffusion sequence may also include an RF pulse block characterized by parameters relating to an RF pulse (e.g., a frequency of the RF pulse, a bandwidth of the RF pulse, etc.) emitted by an RF coil. The at least diffusion block may be arranged subsequent to the RF pulse block in the diffusion sequence.

Figure 10:
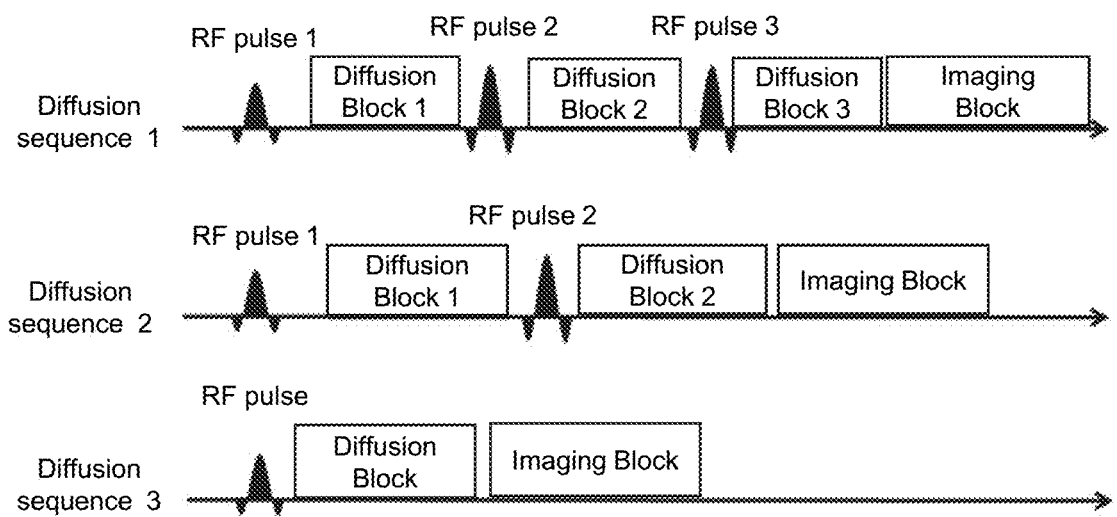
FIG. 10 shows exemplary diffusion sequences according to some embodiments of the present disclosure.

In some embodiments, the diffusion sequence may be constructed based on, for example, an echo planar imaging (EPI) sequence, a fast spin echo (FSE) sequence, etc. In some embodiments, the diffusion sequence may be a single-shot sequence, i.e., an RF pulse may be applied once within a TR. For example, the diffusion sequence may include one single diffusion block and one single imaging block arranged subsequent to the one single RF excitation pulse in the diffusion sequence. In some embodiments, the diffusion sequence may be a multi-shot sequence, i.e., an RF pulse may be applied for multiple times when the diffusion sequence is applied once (i.e., within a TR). For example, the diffusion sequence may include a plurality of diffusion blocks and a plurality of RF pulse blocks. Each of the plurality of diffusion blocks may be arranged subsequent to one of the plurality of RF pulse blocks in the diffusion sequence. The multi-shot sequence may also include an imaging block arranged subsequent to the last one of the plurality of diffusion blocks. As a further example, FIG. 10 shows exemplary diffusion sequences according to some embodiments of the present disclosure. As shown in FIG. 10, diffusion sequence 1 includes three diffusion blocks, diffusion block 1, diffusion block 2, and diffusion block 3, and one image block arranged subsequent to diffusion block 3. Diffusion sequence 1 further includes three RF pulse blocks, RF pulse block 1, RF pulse block 2, and RF pulse block 3. Diffusion block 1 of diffusion sequence 1 is arranged subsequent to RF pulse block 1 including an excitation pulse with a filp angle 90 degrees. Diffusion block 2 of diffusion sequence 1 is arranged subsequent to RF pulse block 2 including a refocusing pulse with a filp angle 180 degrees. Diffusion block 3 of diffusion sequence 1 is arranged subsequent to RF pulse block 3 including an excitation pulse with a filp angle 90 degrees. Diffusion sequence 2 includes two diffusion blocks, diffusion block 1 and diffusion block 2, and one image block arranged subsequent to diffusion block 2. Diffusion sequence 2 further includes two RF pulse blocks, RF pulse 1 and RF pulse 2. Diffusion block 1 of diffusion sequence 2 is arranged subsequent to RF pulse block 1 including an excitation pulse with a filp angle 90 degrees. Diffusion block 2 of diffusion sequence 2 is arranged subsequent to RF pulse block 2 including a refocusing pulse with a filp angle 180 degrees. Diffusion sequence 3 includes one diffusion block and one image block arranged subsequent to the diffusion block. Diffusion sequence 3 further includes one RF pulse block including an excitation pulse with a filp angle 90 degrees. The diffusion block of diffusion sequence 3 is arranged subsequent to the RF pulse block.

In some embodiments, the plurality of groups of imaging data may be acquired both based on the diffusion sequence. Each group of the plurality of groups of imaging data may be generated by applying the diffusion sequence once. The plurality of group of the plurality of groups of imaging data may be generated via scanning the subject by applying the diffusion sequence for several times in a continuous time period. For example, the plurality of groups of imaging data may include a first group of imaging data and a second group of imaging data. The first group of imaging data may be generated via scanning the subject by applying the diffusion sequence once during a first time period. The second group of imaging data may be generated via scanning the subject by applying the diffusion sequence once during a second time period. In some embodiments, the plurality of groups of imaging data may be acquired by applying a plurality of diffusion sequences during a scan. Each group of the plurality of groups of imaging data may be acquired by apply- ing one of the plurality of diffusion sequences. In some embodiments, the count (or number) of diffusion blocks in each of the plurality of diffusion sequences may be different. For example, the plurality of diffusion sequences may include a first diffusion sequence and a second diffusion sequence. The first diffusion sequence may include two diffusion blocks and one imaging block arranged subsequent to the two diffusion blocks. The second diffusion sequence may include one diffusion block and one imaging block arranged subsequent to the one diffusion block.

A specific group of imaging data may include specific k-space data in the k-space domain, a specific MR image in the image domain, etc. For a single-shot diffusion sequence, during the application of the single-shot diffusion sequence once, one single shot of an RF pulse may be applied to generate one or more echo signals (i.e., MR signals). The specific group of imaging data may be generated based on the one or more echo signals corresponding to the one single shot. For example, the one or more echo signals may be used to fill a k-space to generate specific k-space data. The specific k-space data may be designated as the specific group of imaging data. As another example, the specific k-space data may be further used to reconstruct a specific MR image. The specific MR image may be designated as the specific group of imaging data. For a multi-shot diffusion sequence, during the application of the multi-shot diffusion sequence once, a plurality of shots of an RF pulse may be performed. Each of the plurality of shots may generate one or more echo signals (i.e., MR signals). The specific group of imaging data may be generated based on the one or more echo signals corresponding to each of the plurality shots. For example, the one or more echo signals corresponding to each of the plurality shots may be used to fill a k-space to generate k-space data. The specific group of imaging data may be generated by averaging the generated k-space data corresponding to each of the plurality shots. As another example, the generated k-space data corresponding to each of the plurality shots may be used to reconstruct an intermediate image. The specific group of imaging data may be generated by averaging the reconstructed intermediate image corresponding to each of the plurality shots. Thus, the specific group of imaging data may be also referred to as a group of averaged imaging data, such as averaged k-space data, an averaged MR image, etc.

In 520, the processing device 120 (e.g., the correction module 420) (e.g., the processor 210) may determine one or more correction coefficients associated with an error caused by the diffusion sequence for each group of the plurality of groups of imaging data. Each group of the plurality of groups of imaging data may correspond to one or more correction coefficients. In some embodiments, the one or more correction coefficients for a specific group of imaging data may be determined based on the plurality of groups of imaging data in the image domain. The specific group of imaging data in the image domain may be presented as a specific MR image including a plurality of pixels (or voxels). Each of the plurality of pixels (or voxels) may be denoted by a phase and a magnitude. The error caused by the diffusion sequence associated with the specific group of imaging data may include a phase error, a magnitude error, etc. In some embodiments, the one or more correction coefficients for the specific group of imaging data may include a phase correction coefficient configured to correct the phase error associated with the specific group of imaging data, a magnitude correction coefficient configured to correct the magnitude error the specific group of imaging data, etc.

In some embodiments, the processing device 120 may determine a phase correction coefficient corresponding to the specific group of imaging data (e.g., a specific MR image) based on reference imaging data (e.g., a reference MR image). For example, the processing device 120 may identify one group of the plurality of groups of imaging data as the reference imaging data. The reference imaging data may correspond to a maximum magnitude among the plurality of groups of imaging data. The processing device 120 may determine phase difference data between the specific group of imaging data and the reference imaging data. The processing device 120 may further determine the phase correction coefficient corresponding to the specific group of imaging data based on the phase difference data. More descriptions for determining the phase correction coefficient corresponding to a specific group of imaging data may be found elsewhere in the present disclosure (e.g., FIG. 6 and the descriptions thereof).

In some embodiments, the processing device 120 may determine a magnitude correction coefficient corresponding to a specific group of imaging data (e.g., a specific MR image) based on reference imaging data (e.g., a reference MR image). For example, the processing device 120 may identify one group of the plurality of groups of imaging data as the reference imaging data. In some embodiments, the reference imaging data may correspond to a maximum magnitude among the plurality of groups of imaging data. In some embodiments, the reference imaging data may be an average of magnitude data associated with the plurality of groups of imaging data. The processing device 120 may determine similarity data between the specific group of imaging data and the reference imaging data. The processing device 120 may further determine the magnitude correction coefficient corresponding to the specific group of imaging data based on the similarity data. More descriptions for determining the magnitude correction coefficient corresponding to a specific group of imaging data may be found elsewhere in the present disclosure (e.g., FIG. 7 and the descriptions thereof).

In 530, the processing device 120 (e.g., the correction module 420) (e.g., the processor 210) may determine, based on the one or more correction coefficients corresponding to the each group of the plurality of groups of imaging data, a plurality of groups of corrected imaging data.

In some embodiments, the processing device 120 may determine a specific group of corrected imaging data by performing at least one of a phase correction or a magnitude correction on the specific group of imaging data in the image domain. For example, the processing device 120 may perform at least one of the phase correction or the magnitude correction on the specific group of imaging data by performing a dot product between the specific group of imaging data and the one or more corresponding correction coefficients. In some embodiments, a specific group of imaging data in the image domain may include a specific MR image. The specific MR image may be denoted by a magnitude component and a phase component as described by Equation (1):

$$Y_m = A \cdot e^{i\theta}, \quad (1)$$

where $Y_m$ denotes a specific group of imaging data in the image domain acquired at the mth time, A denotes a magnitude component of the specific group of imaging data, and $\theta$ denotes a phase component of the specific group of imaging data. As used herein, the magnitude component of the specific group of imaging data may be denoted by a first matrix including a plurality of elements. Each of the plurality of elements in the first matrix may denote a magnitude of a pixel (or voxel) in the specific MR image. The phase component of the specific group of imaging data may be denoted by a second matrix including a plurality of elements. Each of the plurality of elements in the second matrix may denote a phase of a pixel (or voxel) in the specific MR image.

In some embodiments, the phase correction coefficient corresponding to the specific MR image may be denoted by a phase correction matrix. The phase correction matrix including a plurality of phase correction factors. Each of the plurality of phase correction factors may correspond to a pixel (or voxel) in the specific MR image. The magnitude correction coefficient corresponding to the specific MR image may be denoted by a magnitude correction matrix. The magnitude correction matrix including a plurality of magnitude correction factors. Each of the plurality of magnitude correction factors may correspond to a pixel (or voxel) in the specific MR image. The dot product between the one or more correction coefficients and the specific group of imaging data may be performed by multiplying each of the plurality of phase correction factors with a phase of a corresponding pixel (or voxel) in the specific MR image and/or multiplying each of the plurality of magnitude correction factors with a magnitude of a corresponding pixel (or voxel) in the specific MR image. The corrected imaging data may be expressed as Equation (2):

$$Y'_m = W_m Y_m \cdot e^{i\theta_m}, \quad (2)$$

where $Y'_m$ denotes the corrected imaging data of $Y_m$, $Y_m$ denotes the specific group of imaging data in the image domain acquired at the mth time, $e^{i\theta_m}$ denotes the phase correction coefficient of the specific group of imaging data $Y_m$, and $W_m$ denotes the magnitude correction coefficient of the specific group of imaging data.

In some embodiments, the magnitude correction coefficient of the specific group of imaging data may be also referred to as a weighting coefficient. In some embodiments, the specific MR image in the image domain may be converted into a phase image and/or a magnitude image by extracting the phase component and/or the magnitude component, respectively. The phase correction and/or the magnitude correction may be performed on the phase image and the magnitude image, respectively. For example, the processing device 120 may perform a dot product between the phase image and the phase correction coefficient and/or between the magnitude image and the magnitude correction coefficient. Then the processing device 120 may determine the specific group of corrected imaging data (i.e., corrected MR image) based on the corrected phase image and/or the corrected magnitude image.

In some embodiments, the processing device 120 may determine a specific group of corrected imaging data by performing at least one of a phase correction or a magnitude correction on the specific group of imaging data in the k-space domain. For example, the processing device 120 may perform at least one of the phase correction or the magnitude correction on the specific group of imaging data by performing a convolution operation between the specific group of imaging data and the one or more corresponding correction coefficients. In some embodiments, the specific group of imaging data may include specific k-space data in the k-space domain. The convolution operation between the specific k-space data and the one or more corresponding correction coefficients may be performed by converting the one or more corresponding correction coefficients from the image domain into the k-space domain. For example, the one or more corresponding correction coefficients may be converted from the image domain into the k-space domain by performing a fast Fourier transform (FFT) on the one or more corresponding correction coefficients. Then the convolution operation may be performed between the specific k-space data and the corresponding correction coefficients in the k-space domain to obtain the specific corrected k-space data. In some embodiments, the specific group of corrected imaging data in the image domain may be determined by performing an inverse fast Fourier transformation (FFT) on the specific corrected k-space data.

In 540, the processing device 120 (e.g., the averaging module 430) (e.g., the processor 210) may determine averaged imaging data by averaging the plurality of groups of corrected imaging data in a complex domain. In some embodiments, the plurality of groups of corrected imaging data may be in the image domain. For example, each of the plurality of groups of corrected imaging data may include a corrected MR image. The averaging of the plurality of groups of corrected imaging data in the complex domain may be performed according to Equation (3) as follow:

$$Y = \frac{W_1 \cdot Y_1 \cdot e^{i\phi_1} + W_2 \cdot Y_2 \cdot e^{i\phi_2} + \ldots + W_N \cdot Y_N \cdot e^{i\phi_N}}{(W_1 + W_2 + \ldots + W_N)}, \quad (3)$$

where Y denotes the averaged imaging data, $Y_N$ denotes a specific group of imaging data in the image domain acquired at the Nth time, $e^{i\theta_N}$ denotes the phase correction coefficient corresponding to $Y_N$, and $W_N$ denotes the magnitude correction coefficient corresponding to $Y_N$. In some embodiments, the processing device 120 may perform only the phase correction on the plurality of groups of imaging data, and the magnitude correction coefficient (e.g., $W_N$ in Equation (3)) corresponding to each of the plurality of groups of imaging data may be denoted by a matrix including a plurality of elements equal to 1. In some embodiments, the processing device 120 may perform only the magnitude correction on the plurality of groups of imaging data, and the phase correction coefficient (e.g., $e^{i\theta_N}$ in Equation (3)) corresponding to each of the plurality of groups of imaging data may be denoted by a matrix including a plurality of elements equal to 1. In some embodiments, the processing device 120 may perform only the phase correction on the plurality of groups of imaging data to obtain the plurality of corrected imaging data. The averaged imaging data may be obtained by performing a weighted average on the plurality of corrected imaging data using a plurality of weighting coefficients each of which corresponds to one of the plurality of groups of corrected imaging data. In some embodiments, the processing device 120 may obtain the plurality of groups of corrected imaging data by executing a weighting operation on the plurality of groups of imaging data using weighting coefficients each of which corresponds to one of the plurality of groups of imaging data. In some embodiments, the processing device 120 may designate the magnitude correction coefficient or the phase correction coefficient as the weighting coefficient. The averaged imaging data may be obtained by performing a weighted average on the plurality of groups of corrected imaging data using the weighting coefficients each of which corresponds to one of the plurality of groups of imaging data. In some embodiments, the processing device 120 may obtain averaged imaging data (i.e., corrected imaging data) by executing a weighting operation on the plurality of groups of imaging data using weighting coefficients each of which corresponds to one of the plurality of groups of imaging data. In some embodiments, the processing device 120 may determine the weighting coefficient based on the magnitude correction coefficient and/or the phase correction coefficient. For example, the weighting coefficient corresponding to a specific group of imaging data may be determined by a ratio $$\left(e.g., \frac{W_N \cdot e^{i\phi_N}}{(W_1 + W_2 + \ldots + W_N)}\right)$$

of the magnitude correction coefficient and/or the phase correction coefficient corresponding to a specific group of imaging data and a sum of the magnitude correction coefficient and/or the phase correction coefficient corresponding to each of the plurality of groups of imaging data. In some embodiments, the weighting coefficient may include a plurality of weighting factors. Each of the plurality of weighting factors may correspond to a pixel of each of the plurality of groups of imaging data. A value of a weighting factor may positively correlate with a degree of similarity between the pixel of each of the plurality of groups of imaging data and a corresponding pixel of the reference imaging data. For example, the greater the degree of similarity between the pixel of each of the plurality of groups of imaging data and a corresponding pixel of the reference imaging data is, the greater the value of a weighting factor corresponding to the pixel may be. More descriptions for the degree of similarity between two pixels may be found elsewhere in the present disclosure (e.g., FIG. 7 and the descriptions thereof).

In some embodiments, the weighting coefficients corresponding to some or all of the plurality of groups of imaging data may be determined by a user or corresponding to a default setting of the MRI system 100.

In some embodiments, the plurality of groups of corrected imaging data may be in the k-space domain. For example, each of the plurality of groups of corrected imaging data may include corrected k-space data. The averaging of the plurality of groups of corrected imaging data in the complex domain may be performed according to Equation (4) as follow:

$$Y = \frac{F^{-1}\left(FW_1 \otimes Y_1 \otimes Fe^{i\phi_1} + FW_2 \otimes Y_2 \otimes Fe^{i\phi_2} + \ldots + FW_N \otimes Y_N \otimes Fe^{i\phi_N}\right)}{(W_1 + W_2 + \ldots + W_N)}, \quad (4)$$

where Y denotes the averaged imaging data, $Y_N$ denotes a specific group of imaging data in the k-space domain acquired at the Nth time, $e^{i\theta_N}$ denotes the phase correction coefficient corresponding to $Y_N$, F denotes a Fourier transform, $F^{-1}$ denotes an inverse Fourier transform, $\otimes$ denotes a convolution operation, and $W_N$ denotes the magnitude correction coefficient corresponding to $Y_N$. In some embodiments, the plurality of groups of corrected imaging data may be in the k-space domain. For example, each of the plurality of groups of corrected imaging data may include corrected k-space data. The plurality of groups of corrected k-space data may be averaged in the k-space domain to obtain average k-space data.

In 550, the processing device 120 (e.g., the generation module 440) (e.g., the processor 210) may generate a target MR image based on the averaged imaging data. The target MR image may be also referred to as a diffusion image. In some embodiments, the processing device 120 may generate the target MR image by converting the averaged imaging data in the k-space domain (i.e., average k-space data) into averaged imaging data the imaging domain. For example, the processing device 120 may perform a Fourier transform (FT) on the averaged imaging data in the k-space domain. In some embodiments, the processing device 120 may designate the averaged imaging data in the image domain as the target MR image.

It should be noted that the above description regarding the process 500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 500 may include one or more additional operations or one or more of the operations mentioned above may be omitted. For example, operation 540 and operation 550 may be integrated into one operation. As another example, the process 500 may include one or more additional operations (e.g., one or more operations of process 600) to determine one or more correction coefficients. In some embodiments, operation 530 and operation 540 may be integrated into one single operation. For example, the averaged imaging data may be determined by weighting the plurality of groups of imaging data based on a plurality of weighting coefficients as described elsewhere in the present disclosure.

Figure 6:
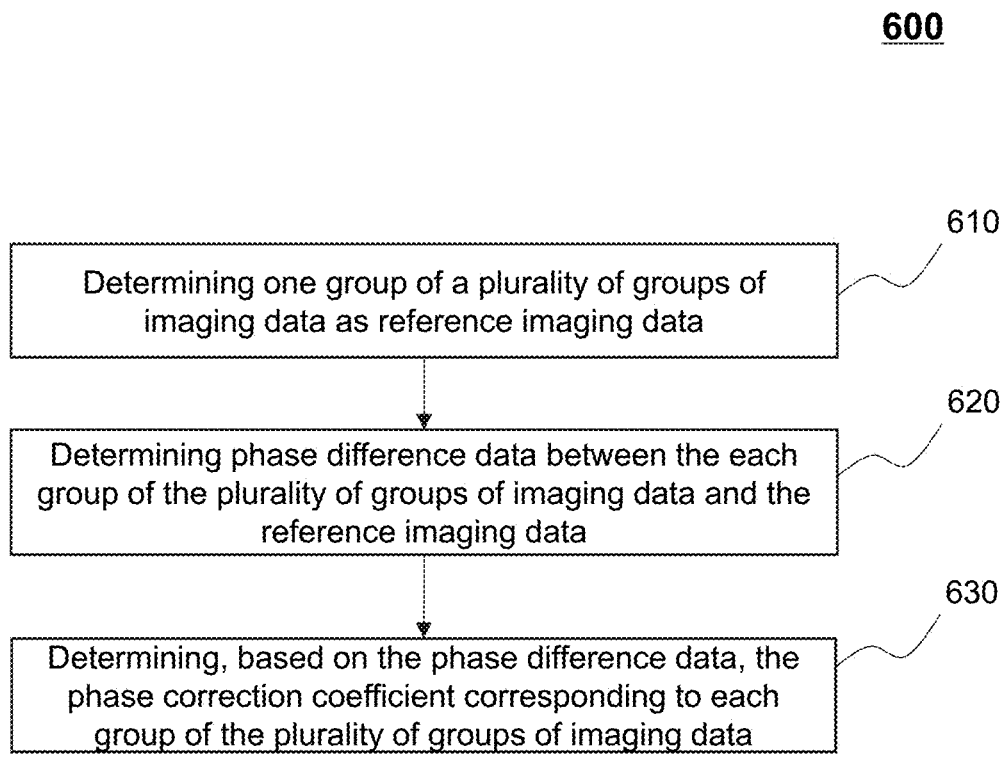
FIG. 6 is a flowchart of an exemplary process for determining a phase correction coefficient according to some embodiments of the present disclosure.

FIG. 6 is a flowchart of an exemplary process for determining a phase correction coefficient according to some embodiments of the present disclosure. The process 600 may be executed by the processing device 120. For example, the process 600 may be implemented as a set of instructions (e.g., an application) stored in the storage, e.g., storage 220, the storage device 130, the storage 390, a storage device external to and accessible by the MRI system 100. The processing device 120, the processor 210, and the CPU 340, may execute the set of instructions, and when executing the instructions, it may be configured to perform the process 600. The operations of the process 600 presented below are intended to be illustrative. In some embodiments, the process may be accomplished with one or more additional operations not described, and/or without one or more of the operations discussed. Additionally, the order in which the operations of the process 600 as illustrated in FIG. 6 and described below is not intended to be limiting. At least one portion of operation 520 may be performed according to process 600.

In 610, the processing device 120 (e.g., the correction module 420) (e.g., the processor 210) may determine one group of a plurality of groups of imaging data as reference imaging data. The plurality of groups of imaging data may be obtained as described in connection with operation 510 as described in FIG. 5. Each group of the plurality of groups of imaging data may include an MR image in the image domain. The MR image may include a plurality of first pixels (or voxels). Each of the plurality of first pixels (or voxels) may be denoted by a first phase and a first magnitude in the complex domain.

In some embodiments, the processing device 120 may identify the one group of the plurality of groups of imaging data that corresponds to a maximum magnitude among the plurality of groups of imaging data as the reference imaging data. For example, the processing device 120 may calculate a sum of the first magnitudes of the plurality of first pixels (or voxels) in the MR image corresponding to each group of the plurality of groups of imaging data. The processing device 120 may compare the sums of the first magnitudes corresponding to the plurality of groups of imaging data to identify the maximum sum of the first magnitudes among the plurality of groups of imaging data, and designate the group of imaging data corresponding to the maximum sum as the reference imaging data. As another example, the processing device 120 may calculate a mean of the first magnitudes of the plurality of first pixels (or voxels) in the MR image corresponding to each group of the plurality of groups of imaging data. The processing device 120 may compare the means of the first magnitudes corresponding to the plurality of groups of imaging data to identify the maximum mean of the first magnitudes among the plurality of groups of imaging data, and designate the group of imaging data corresponding to the maximum mean as the reference imaging data.

In 620, the processing device 120 (e.g., the correction module 420) (e.g., the processor 210) may determine phase difference data between the each group of the plurality of groups of imaging data and the reference imaging data. The reference imaging data may include a reference MR image. The reference MR image may include a plurality of second pixels (or voxels). Each of the plurality of second pixels (or voxels) may be denoted by a second phase and a second magnitude in the complex domain. The phase difference data between a specific group of the plurality of groups of imaging data (i.e., a specific group of imaging data) and the reference imaging data may include a plurality of phase differences. Each of the plurality of phase differences may include a difference between phases of a first pixel (or voxel) in the specific group of imaging data (i.e., a specific MR image) and a corresponding second pixel (or voxel) in the reference imaging data (i.e., the reference image). As used herein, a first pixel (or voxel) in a specific group of imaging data corresponding to a second pixel (or voxel) in the reference imaging data may refer to that the first pixel (or voxel) and the corresponding second pixel (or voxel) correspond to a same spatial location of a subject or a same position in the specific group of imaging data and the reference imaging data, respectively.

In some embodiments, the specific group of imaging data may be expressed as a matrix (i.e., matrix A). The rows and the columns of the matrix may denote positions of the plurality of first pixels (or voxels) of the specific group of imaging data. And values of elements in the matrix A may denote values of first phases of the plurality of first pixels (or voxels) in the specific group of imaging data. In some embodiments, the reference imaging data may be expressed as another matrix (i.e., matrix B). The rows and the columns of the matrix B may denote positions of the plurality of second pixels (or voxels) of the reference imaging data. And values of elements in the matrix B may denote values of the second phases of the plurality of second pixels (or voxels) in the reference imaging data. The phase difference data for the specific group of imaging data may be generated by performing a subtraction operation between the matrix A and the matrix B.

In 630, the processing device 120 (e.g., the correction module 420) (e.g., the processor 210) may determine the phase correction coefficient corresponding to each group of the plurality of groups of imaging data based on the phase difference data. The phase correction coefficient corresponding to a specific group of imaging data may be denoted by a phase correction matrix including a plurality of phase correction factors. Each of the plurality of phase correction factors may correspond to one of the plurality of first pixels (or voxels) in the specific group of imaging data.

In some embodiments, the processing device 120 may designate the phase difference data obtained in operation 620 as the phase correction coefficient. In some embodiments, the processing device 120 may perform a denoising operation on the phase difference data obtained in 620 to obtain denoised phase difference data. The processing device 120 may designate the denoised phase difference data as the phase correction coefficient. Exemplary denoising operations may include using a spatial-domain filter, a transform-domain filter, a morphological noise filter, or the like, or a combination thereof. For example, the spatial-domain filter may include a Gaussian mean filter, a median filter, a maximum filter, a minimum filter, etc. The transform-domain filter may include a lowpass filter, a high-pass filter, etc.

In some embodiments, process 600 may further include determining a weighting coefficient corresponding to each of the plurality of groups of imaging data based on the phase correction coefficient. For example, the weighting coefficient corresponding to a specific group of imaging data may be determined based on a ratio between the phase correction coefficient corresponding to the specific group of imaging data and a sum of matrixes corresponding to the plurality of groups of imaging data. In some embodiments, each of the matrixes may correspond to one of the plurality of groups of imaging data. Each of the matrixes may include a plurality of elements, for example, equal to 1.

It should be noted that the above description regarding the process 500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, process 600 may further include an operation for denoising the phase difference data after operation 620.

Figure 7:
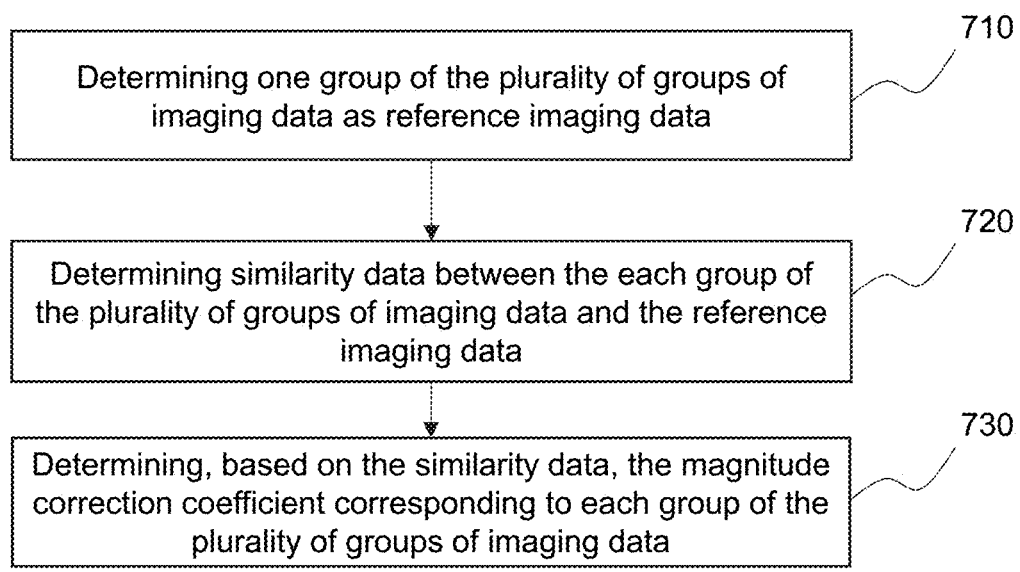
FIG. 7 is a flowchart of an exemplary process for determining a magnitude correction coefficient according to some embodiments of the present disclosure.

FIG. 7 is a flowchart of an exemplary process for determining a magnitude correction coefficient according to some embodiments of the present disclosure. The process 700 may be executed by the processing device 120. For example, the process 700 may be implemented as a set of instructions (e.g., an application) stored in the storage, e.g., storage 220, the storage device 130, the storage 390, a storage device external to and accessible by the MRI system 100. The processing device 120, the processor 210, and the CPU 340, may execute the set of instructions, and when executing the instructions, it may be configured to perform the process 700. The operations of the process 700 presented below are intended to be illustrative. In some embodiments, the process may be accomplished with one or more additional operations not described, and/or without one or more of the operations discussed. Additionally, the order in which the operations of the process 700 as illustrated in FIG. 7 and described below is not intended to be limiting. At least one portion of operation 520 may be performed according to the process 700.

In 710, the processing device 120 (e.g., the correction module 420) (e.g., the processor 210) may determine one group of the plurality of groups of imaging data as reference imaging data. The plurality of groups of imaging data may be obtained as described in connection with operation 510 as described in FIG. 5. Each group of the plurality of groups of imaging data may include an MR image in the image domain. The MR image may include a plurality of first pixels (or voxels). Each of the plurality of first pixels (or voxels) may be denoted by a first phase and a first magnitude in a complex domain. In some embodiments, the processing device 120 may identify the one group of the plurality of groups of imaging data that corresponds to a maximum magnitude among the plurality of groups of imaging data as the reference imaging data. For example, the processing device 120 may calculate a sum of the first magnitudes of the plurality of first pixels (or voxels) in the MR image corresponding to each group of the plurality of groups of imaging data. The processing device 120 may compare the sums of the first magnitudes corresponding to the plurality of groups of imaging data to identify the maximum sum of the first magnitudes among the plurality of groups of imaging data, and designate the group of imaging data corresponding to the maximum sum as the reference imaging data. As another example, the processing device 120 may calculate a mean of the first magnitudes of the plurality of first pixels (or voxels) in the MR image corresponding to each group of the plurality of groups of imaging data. The processing device 120 may compare the means of the first magnitudes of the plurality of first pixels (or voxels) in the MR image corresponding to the plurality of groups of imaging data to identify the maximum mean of the first magnitudes among the plurality of groups of imaging data, and designate the group of imaging data corresponding to the maximum mean as the reference imaging data.

In some embodiments, the processing device 120 may determine an average of magnitude data associated with the plurality of groups of imaging data, and designate the average of the magnitude data associated with the plurality of groups of imaging data as the reference imaging data. Specifically, each group of the plurality of groups of imaging data may be expressed as a matrix. The rows and the columns of the matrix may denote positions of the plurality of first pixels (or voxels) of the each group of the plurality of groups of imaging data. And the value of elements in the matrix may denote values of the first magnitudes of the plurality of first pixels (or voxels) in the each group of the plurality of groups of imaging data. The processing device 120 may obtain the magnitude data associated with the plurality of groups of imaging data by performing an additive operation on the matrixes corresponding to the plurality of groups of imaging data. The processing device 120 may further determine the average of the magnitude data. Then the processing device 120 may designate the average of the magnitude data associated with the plurality of groups of imaging data as the reference imaging data.

In 720, the processing device 120 (e.g., the correction module 420) (e.g., the processor 210) may determine similarity data between the each group of the plurality of groups of imaging data and the reference imaging data. The reference imaging data may include a reference MR image. The reference MR image may include a plurality of second pixels (or voxels). Each of the plurality of second pixels (or voxels) may be denoted by a second phase and a second magnitude in the complex domain. The similarity data between a specific group of the plurality of groups of imaging data (i.e., a specific group of imaging data) and the reference imaging data may include a plurality of similarity elements. Each of the plurality of similarity elements may correspond to a first pixel (or voxel) in the specific group of imaging data (i.e., a specific MR image) and a corresponding second pixel (or voxel) in the reference imaging data (i.e., the reference image). Each of the plurality of similarity elements may denote a degree of similarity between a first pixel (or voxel) in the specific group of imaging data (i.e., a specific MR image) and a corresponding second pixel (or voxel) in the reference imaging data (i.e., the reference image). As used herein, a first pixel (or voxel) in the specific group of imaging data corresponding to a second pixel (or voxel) in the reference imaging data may refer to that the first pixel (or voxel) and the corresponding second pixel (or voxel) correspond to a same spatial location or portion of a subject or a same position in the specific group of imaging data and the reference imaging data, respectively.

In some embodiments, the similarity data between a specific group of the plurality of groups of imaging data and the reference imaging data may be determined in the image domain. For example, a similarity element between a first pixel (or voxel) in the specific group of imaging data (i.e., a specific MR image) and a corresponding second pixel (or voxel) in the reference imaging data (i.e., the reference image) may be determined based on pixel (or voxel) values of the first pixel (or voxel) in the specific group of imaging data (i.e., a specific MR image) and of the corresponding second pixel (or voxel) in the reference imaging data (i.e., the reference image). The processing device 120 may compare pixel (or voxel) values of the first pixel (or voxel) and of the corresponding second pixel (or voxel). The smaller a difference between the pixel (or voxel) values of the first pixel (or voxel) and of the corresponding second pixel (or voxel) is, the greater the similarity element between the first pixel (or voxel) and the corresponding second pixel (or voxel) may be.

In some embodiments, the processing device 120 may determine the similarity data between the each group of the plurality of groups of imaging data and the reference imaging data in the magnitude domain. For example, the processing device 120 may determine the similarity data between a specific group of imaging data and the reference imaging data based on magnitude difference data between the specific group of imaging data and the reference imaging data. The magnitude difference data between the specific group of imaging data and the reference imaging data may include a plurality of magnitude differences. Each of the plurality of magnitude differences may correspond to a first pixel (or voxel) in the specific group of imaging data (i.e., a specific MR image) and a corresponding second pixel (or voxel) in the reference imaging data (i.e., the reference image). As a further example, the processing device 120 may compare magnitudes of the first pixel (or voxel) and the corresponding second pixel (or voxel) to determine a magnitude difference of the first pixel (or voxel) relative to the corresponding second pixel (or voxel). The processing device 120 may determine a similarity element of the first pixel (or voxel) relative to a corresponding second pixel (or voxel) based on the magnitude difference between the first pixel (or voxel) and the corresponding second pixel (or voxel). The smaller the magnitude difference between the first pixel (or voxel) and the corresponding second pixel (or voxel) is, the greater the similarity element of the first pixel (or voxel) relative to the corresponding second pixel (or voxel) may be.

In some embodiments, the processing device 120 may perform a denoising operation on the magnitude difference data to obtain denoised magnitude difference data. The processing device 120 may determine the similarity data based on the denoised magnitude difference data. Exemplary denoising operations may include using a spatial-domain filter, a transform-domain filter, a morphological noise filter, or the like, or a combination thereof. For example, the spatial-domain filter may include a Gaussian mean filter, a median filter, a maximum filter, a minimum filter, etc. The transform-domain filter may include a lowpass filter, a high-pass filter, etc.

In 730, the processing device 120 (e.g., the correction module 420) (e.g., the processor 210) may determine a magnitude correction coefficient corresponding to each group of the plurality of groups of imaging data based on the similarity data. The magnitude correction coefficient corresponding to a specific group of imaging data may be denoted by a magnitude correction matrix including a plurality of magnitude correction factors. Each of the plurality of magnitude correction factors may correspond to one of the plurality of first pixels (or voxels) in the specific group of imaging data.

In some embodiments, the similarity data between the specific group of imaging data and the reference imaging data may include a plurality of similarity elements. Each of the plurality of similarity elements may correspond to a first pixel (or voxel) of the specific group of imaging data. The processing device 120 may determine the magnitude correction factor corresponding to a first pixel (or voxel) of the specific group of imaging data based on the similarity element corresponding to the first pixel (or voxel) of the specific group of imaging data. The greater the similarity element corresponding to the first pixel (or voxel) is, the greater the magnitude correction factor corresponding to the first pixel (or voxel) may be. In some embodiments, the processing device 120 may perform a denoising operation on the similarity data to obtain denoised similarity data. The processing device 120 may determine the magnitude correction coefficient based on the denoised similarity data.

In some embodiments, process 700 may further include determine a weighting coefficient corresponding to each of the plurality of groups of imaging data based on the magnitude correction coefficient. For example, the weighting coefficient corresponding to a specific group of imaging data may be determined based on a ratio between the magnitude correction coefficient corresponding to the specific group of imaging data and a sum of the magnitude correction coefficients corresponding to the plurality of groups of imaging data.

It should be noted that the above description regarding the process 500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, process 700 may include performing a denoising operation on the similarity data after operation 720.

EXAMPLES

The examples are provided for illustration purposes, and not intended to limit the scope of the present disclosure.

Example 1

Exemplary MR Brain Images of a Patient

Figure 8:
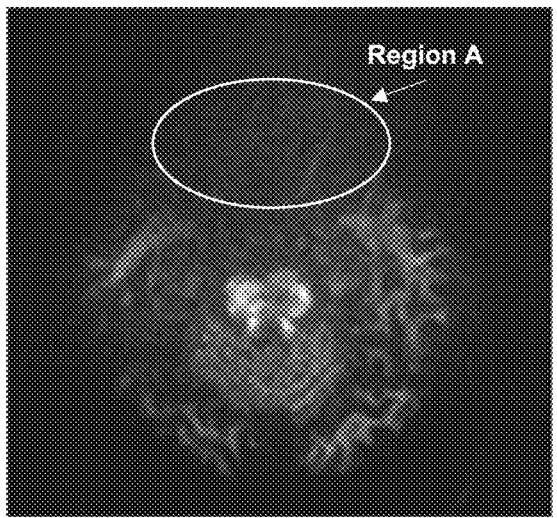
FIG. 8 shows exemplary MR brain images of a patient according to some embodiments of the present disclosure.
Figure 8:
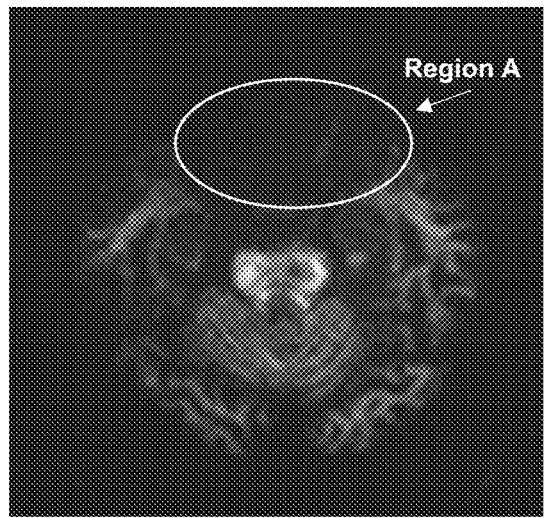

FIG. 8 shows exemplary MR brain images of a patient according to some embodiments of the present disclosure.

As illustrated in FIG. 8, Image 1 and image 2 were reconstructed based on the same imaging data acquired by applying an echo planar imaging (EPI) sequence for 10 times. The imaging data for reconstructing Image 1 and Image 2 corresponded to a diffusion sensitivity coefficient (i.e., b value) of 10000 that was determined based on a diffusion gradient. The higher the b value is, the smaller the SNR may be, and the greater the contrast between different types of tissue may be. Image 1 was reconstructed based on an average algorithm in the magnitude domain. Image 2 was reconstructed according to process 500 as described in FIG. 5. Image 1 shows more noises than Image 2, for example, in Region A. In other words, the signal to noise ratio (SNR) of Image 2 exceeds that of Image 1.

Example 2

Exemplary MR Prostate Images of a Patient

Figure 9:
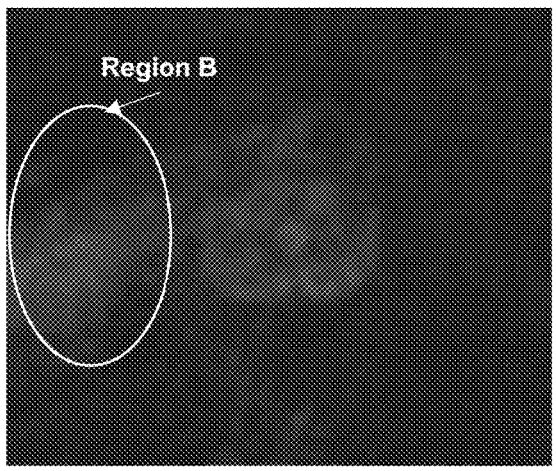
FIG. 9 shows exemplary MR prostate images of a patient according to some embodiments of the present disclosure.
Figure 9:
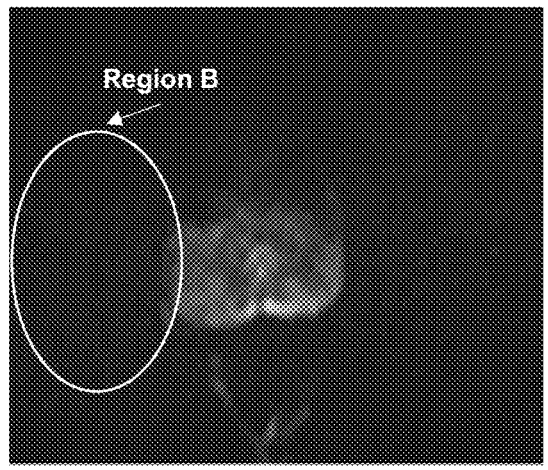

FIG. 9 shows exemplary MR prostate images of a patient according to some embodiments of the present disclosure. As illustrated in FIG. 9, Image 1 and image 2 were reconstructed based on the same imaging data acquired using an echo planar imaging (EPI) sequence for 12 times. The imaging data for reconstructing Image 1 and Image 2 corresponded to a diffusion sensitivity coefficient (i.e., b value) of 1500 that was determined based on a diffusion gradient. Image 1 shows more noises than Image 2, for example, in Region B. In other words, the signal to noise ratio (SNR) of Image 2 exceeds that of Image 1. According to the FIG. 8 and FIG. 9, the methods for diffusion MRI as described elsewhere in the present disclosure (e.g., FIG. 5 and the description thereof) may reduce noises to improve the SNR of a diffusion MR image, which may improve image quality even though b value is high.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a specific feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the specific features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

What is claimed is:

1. A system for magnetic resonance imaging (MRI), comprising:
    at least one storage device storing executable instructions, and
    at least one processor in communication with the at least one storage device, when executing the executable instructions, causing the system to perform operations including:
        obtaining a plurality of groups of imaging data, each group of the plurality of groups of imaging data being generated based on MR signals acquired by an MR scanner via scanning a subject using a diffusion sequence;
        for each group of the plurality of groups of imaging data, determining one or more correction coefficients, wherein the one or more correction coefficients include a phase correction coefficient, and wherein to determine one or more correction coefficients, the at least one processor is directed to cause the system to perform additional operations including:
            determining one group of the plurality of groups of imaging data as reference imaging data;
            determining phase difference data between the each group of the plurality of groups of imaging data and the reference imaging data; and
            determining, based on the phase difference data, the phase correction coefficient;
        determining, based on the one or more correction coefficients corresponding to the each group of the plurality of groups of imaging data, a plurality of groups of corrected imaging data;
        determining averaged imaging data by averaging the plurality of groups of corrected imaging data in a complex domain; and
        generating, based on the averaged imaging data, an MR image.

2. The system of claim 1, wherein the one or more correction coefficients further include a magnitude correction coefficient configured to correct a magnitude error.

3. The system of claim 2, wherein to determine one or more correction coefficients, the at least one processor is directed to cause the system to perform additional operations including:
    determining one group of the plurality of groups of imaging data as reference imaging data;
    determining similarity data between the each group of the plurality of groups of imaging data and the reference imaging data; and
    determining, based on the similarity data, the magnitude correction coefficient.

4. The system of claim 3, wherein to determine one group of the plurality of groups of imaging data as reference imaging data, the at least one processor is directed to cause the system to perform additional operations including:
    identifying the one group of imaging data that corresponds to a maximum magnitude among the plurality of groups of imaging data as the reference imaging data.

5. The system of claim 3, wherein to determine one group of the plurality of groups of imaging data as reference imaging data, the at least one processor is directed to cause the system to perform additional operations including:
    determining an average of magnitude data associated with the plurality of groups of imaging data; and
    designating the average of the magnitude data associated with the plurality of groups of imaging data as the reference imaging data.

6. The system of claim 3, wherein to determine, based on the similarity data, the magnitude correction coefficient, the at least one processor is further configured to cause the system to perform additional operations including:
    performing a lowpass filtering operation on the similarity data; and
    determining, based on the filtered similarity data, the magnitude correction coefficient.

7. The system of claim 1, wherein to determine, based on the one or more correction coefficients corresponding to the each group of the plurality of groups of imaging data, a plurality of groups of corrected imaging data, the at least one processor is further configured to cause the system to perform additional operations including:
    performing a dot product between the each group of the plurality of groups of imaging data and the one or more corresponding correction coefficients in an image domain.

8. The system of claim 1, wherein to determine, based on the one or more correction coefficients corresponding to the each group of the plurality of groups of imaging data, a plurality of groups of corrected imaging data, the at least one processor is further configured to cause the system to perform additional operations including:
    performing a convolution operation between the each group of the plurality of groups of imaging data and the one or more corresponding correction coefficients in a k-space domain.

9. The system of claim 1, wherein to determine one group of the plurality of groups of imaging data as reference imaging data, the at least one processor is directed to cause the system to perform additional operations including:
    identifying the one group of the plurality of groups of imaging data that corresponds to a maximum magnitude among the plurality of groups of imaging data as the reference imaging data.

10. The system of claim 1, wherein to determine, based on the phase difference data, the phase correction coefficient, the at least one processor is further configured to cause the system to perform additional operations including:
    performing a lowpass filtering operation on the phase difference data to obtain filtered phase difference data; and
    designating the filtered phase difference data as the phase correction coefficient.

11. The system of claim 1, wherein the diffusion sequence includes at least one diffusion block associated with a diffusion gradient and at least one imaging block associated with one or more scanning parameters, the imaging block being arranged subsequent to the diffusion block in the diffusion sequence.

12. A system for magnetic resonance imaging (MRI), comprising:
    at least one storage device storing executable instructions, and
    at least one processor in communication with the at least one storage device, when executing the executable instructions, causing the system to perform operations including:

obtaining a plurality of groups of imaging data, each group being generated via scanning a subject using a diffusion sequence;

for each group of the plurality of groups of imaging data, determining a weighting coefficient, wherein the weighting coefficient is determined at least based on a phase correction coefficient, and wherein to determine the weighting coefficient, the at least one processor is directed to cause the system to perform additional operations including:

determining one group of the plurality of groups of imaging data as reference imaging data;

determining phase difference data between the each group of the plurality of groups of imaging data and the reference imaging data; and determining, based on the phase difference data, the phase correction coefficient;

determining corrected imaging data by weighting the plurality of groups of imaging data based on the weighting coefficient; and generating a diffusion image of the subject based on the corrected imaging data.

13. The system of claim 12, wherein the weighting coefficient is further determined based on a magnitude correction coefficient configured to correct a magnitude error of each group of imaging data.

14. The system of claim 13, wherein the magnitude correction coefficient is determined based on reference imaging data, and wherein the reference imaging data is a group of imaging data that corresponds to a maximum magnitude among the plurality of groups of imaging data, or the reference imaging data is an average of magnitude data associated with the plurality of groups of imaging data.

15. The system of claim 14, wherein the weighting coefficient includes a plurality of weighting factors, each of the plurality of weighting factors corresponding to a pixel of each of the plurality of groups of imaging data, and a value of a weighting factor positively correlates with a degree of similarity between the pixel of each of the plurality of groups of imaging data and a corresponding pixel of the reference imaging data.

16. The system of claim 14, wherein to determine the magnitude correction coefficient, the at least one processor is directed to cause the system to perform additional operations including:

determining similarity data between each group of the plurality of groups of imaging data and the reference imaging data; and determining, based on the similarity data, the magnitude correction coefficient.

17. The system of claim 14, wherein the weighting coefficient is determined based on a ratio of at least one of the magnitude correction coefficient or the phase correction coefficient and at least one of a sum of magnitude correction coefficients or a sum of phase correction coefficients corresponding to the plurality of groups of imaging data.

18. A method for magnetic resonance imaging (MRI), implemented on a computing device having one or more processors and one or more storage media, the method comprising:

obtaining a plurality of groups of imaging data, each group of the plurality of groups of imaging data being generated based on MR signals acquired by an MR scanner via scanning a subject using a diffusion sequence;

for each group of the plurality of groups of imaging data, determining one or more correction coefficients, wherein the one or more correction coefficients include a phase correction coefficient and determining the one or more correction coefficients including:

determining one group of the plurality of groups of imaging data as reference imaging data;

determining phase difference data between the each group of the plurality of groups of imaging data and the reference imaging data; and determining, based on the phase difference data, the phase correction coefficient;

determining, based on the one or more correction coefficients corresponding to the each group of the plurality of groups of imaging data, a plurality of groups of corrected imaging data;

determining averaged imaging data by averaging the plurality of groups of corrected imaging data in a complex domain; and generating, based on the averaged imaging data, an MR image.

* * * * *